United States Patent
Iwasaki et al.

(10) Patent No.: US 9,924,854 B2
(45) Date of Patent: Mar. 27, 2018

(54) IMAGE PICKUP APPARATUS WITH MAGNETICALLY MOVABLE LENS

(71) Applicant: OLYMPUS CORPORATION, Tokyo (JP)

(72) Inventors: Seiji Iwasaki, Iruma (JP); Takehiko Iguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/357,238

(22) Filed: Nov. 21, 2016

(65) Prior Publication Data

US 2017/0065157 A1 Mar. 9, 2017

Related U.S. Application Data

(63) Continuation of application No. PCT/JP2015/061270, filed on Apr. 10, 2015.

(30) Foreign Application Priority Data

May 22, 2014 (JP) .................................. 2014-106389

(51) Int. Cl.
  *A61B 1/05* (2006.01)
  *A61B 1/00* (2006.01)
  (Continued)

(52) U.S. Cl.
  CPC ............ *A61B 1/00188* (2013.01); *A61B 1/00* (2013.01); *A61B 1/00158* (2013.01); *A61B 1/04* (2013.01);
  (Continued)

(58) Field of Classification Search
  CPC ......... A61B 1/00188; A61B 1/00; A61B 1/05; G02B 7/04; G02B 23/243; G02B 23/24; G02B 23/2438; H04N 5/2254
  See application file for complete search history.

(56) References Cited

U.S. PATENT DOCUMENTS

| 6,099,467 | A | * | 8/2000 | Kehr | .................. | A61B 1/00188 |
| | | | | | | 359/822 |
| 2008/0272869 | A1 | * | 11/2008 | Takayama | .......... | A61B 1/00188 |
| | | | | | | 335/219 |

(Continued)

FOREIGN PATENT DOCUMENTS

| JP | S57-108806 A | 7/1982 |
| JP | H10-225438 A | 8/1998 |

(Continued)

OTHER PUBLICATIONS

International Search Report dated Jul. 7, 2015 issued in PCT/JP2015/061270.

(Continued)

*Primary Examiner* — John P Leubecker
(74) *Attorney, Agent, or Firm* — Scully, Scott, Murphy & Presser, P.C.

(57) ABSTRACT

An image pickup apparatus includes: a lens frame internally holding a movable lens, and including a magnet provided on an outer circumferential surface; a holding frame; and a magnetic member, in which the magnet includes a plurality of magnet pairs provided at uniform angles in a circumferential direction of the lens frame, each of the magnet pairs including magnets that are respectively disposed on distal end side and proximal end side along the optical axis direction of the movable lens, the magnet disposed on the distal end side has a polarity opposite in the radial direction to a polarity of the magnet disposed on the proximal end side, and the magnetic member is provided to face the magnets that configure one of the plurality of magnet pairs.

8 Claims, 15 Drawing Sheets

(51) Int. Cl.
  *G02B 7/04* (2006.01)
  *A61B 1/04* (2006.01)
  *G01D 5/12* (2006.01)
  *G03B 13/34* (2006.01)
  *H04N 5/225* (2006.01)
  *G02B 23/24* (2006.01)

(52) U.S. Cl.
  CPC ............... *G01D 5/12* (2013.01); *G02B 7/04* (2013.01); *G02B 23/2446* (2013.01); *G03B 13/34* (2013.01); *H04N 5/2254* (2013.01); *A61B 1/05* (2013.01); *G02B 23/243* (2013.01); *G02B 23/2438* (2013.01); *H04N 2005/2255* (2013.01)

(56) References Cited

U.S. PATENT DOCUMENTS

| | | | |
|---|---|---|---|
| 2009/0073585 A1 | 3/2009 | Yamashita | |
| 2010/0328791 A1* | 12/2010 | Jung | G03B 17/02 359/824 |
| 2011/0210689 A1* | 9/2011 | Vogel | A61B 1/00188 318/631 |
| 2013/0314517 A1* | 11/2013 | Makiyama | A61B 1/045 348/65 |
| 2015/0160470 A1* | 6/2015 | Terajima | G02B 27/646 359/557 |
| 2015/0287508 A1* | 10/2015 | Wieters | A61B 17/00 335/253 |
| 2016/0374543 A1* | 12/2016 | Wieters | A61B 1/00071 600/167 |

FOREIGN PATENT DOCUMENTS

| | | |
|---|---|---|
| JP | 2002-189162 A | 7/2002 |
| JP | 2005-275269 A | 10/2005 |
| JP | 2005-309076 A | 11/2005 |
| JP | 2006-276565 A | 10/2006 |
| JP | 4642053 B2 | 3/2011 |
| JP | 2013-011749 A | 1/2013 |
| JP | 2013-076910 A | 4/2013 |
| JP | 2013-222116 A | 10/2013 |
| WO | WO 2013/054787 A1 | 4/2013 |

OTHER PUBLICATIONS

Japanese Office Action dated Feb. 9, 2016 issued in Japanese Patent Application No. 2015-557673.

Extended Supplementary European Search Report dated Nov. 24, 2017 in European Patent Application No. 15 79 6326.5.

* cited by examiner

IMAGE PICKUP APPARATUS WITH MAGNETICALLY MOVABLE LENS

CROSS REFERENCE TO RELATED APPLICATION

This application is a continuation application of PCT/JP2015/061270 filed on Apr. 10, 2015 and claims benefit of Japanese Application No. 2014-106389 filed in Japan on May 22, 2014, the entire contents of which are incorporated herein by this reference.

BACKGROUND OF INVENTION

1. Field of the Invention

The present invention relates to an image pickup apparatus and an endoscope that internally hold a movable lens and include a lens frame provided with a magnet on an outer circumferential surface.

2. Description of the Related Art

An image pickup apparatus that internally holds a movable lens, and includes a movable lens frame is well-known. The movable lens frame that is movable forward and backward in an optical axis direction of the movable lens in a holding frame, thereby allowing the image pickup apparatus to switch over a focal point on an object. Note that, for example, the image pickup apparatus is provided in an insertion section of an endoscope.

A configuration of the movable lens frame that is movable in the holding frame with use of a motor or the like is well-known.

Japanese Patent Application Laid-Open Publication No. 57-108806 discloses a configuration of an image pickup apparatus. The image pickup apparatus includes a magnet provided on an outer circumferential surface of a movable lens frame, includes an electromagnetic coil provided at a position, facing the magnet, on an inner circumferential surface of a holding frame, and uses a voice coil motor that moves the movable lens frame in the optical axis direction by Fleming's left-hand rule in response to magnetic field generated between the magnet and the electromagnetic coil that is fed with a current.

Incidentally, to make the movable lens frame movable in the holding frame, a gap is provided between the outer circumferential surface of the movable lens frame and the inner circumferential surface of the holding frame.

In the image pickup apparatus disclosed in Japanese Patent Application Laid-Open Publication No. 57-108806 or in a typical movable configuration of a movable lens frame using a voice coil motor, a magnetic field is applied to the entire outer circumferential surface of the magnet of the movable lens frame from a plurality of directions in a radial direction of the holding frame by the electromagnetic coil.

SUMMARY OF THE INVENTION

An image pickup apparatus according to an aspect of the present invention to achieve the above-described object, includes: a lens frame internally holding a movable lens, and including a magnet provided on an outer circumferential surface; a holding frame holding an objective lens on a distal end, internally holding the lens frame movably in an optical axis direction of the movable lens, and including a coil that is wound on an outer circumferential surface, the coil being provided to face the magnet and generating driving force with respect to the lens frame in response to energization; and a magnetic member provided on outside of the outer circumferential surface of the holding frame in a radial direction of the holding frame that is orthogonal to the optical axis direction, the magnetic member facing the magnet only in one direction of a plurality of directions configuring the radial direction, and the magnetic member generating attracting force with respect to the magnet. The magnet includes a plurality of magnet pairs provided at uniform angles in a circumferential direction of the lens frame, each of the magnet pairs includes magnets that are respectively disposed on distal end side and proximal end side along the optical axis direction of the movable lens. The magnet disposed on the distal end side has a polarity opposite in the radial direction to a polarity of the magnet disposed on the proximal end side. The magnetic member is provided to face the magnets that configure one of the plurality of magnet pairs.

Also, an endoscope according to an aspect of the present invention is an endoscope including the above-described image pickup apparatus, in which the movable member moves in the optical axis direction to switch over a focal point on an object.

DETAILED DESCRIPTION OF THE PREFERRED EMBODIMENT(S)

Hereinafter, some embodiments of the present invention are described with reference to drawings.

First Embodiment

Figure 1:
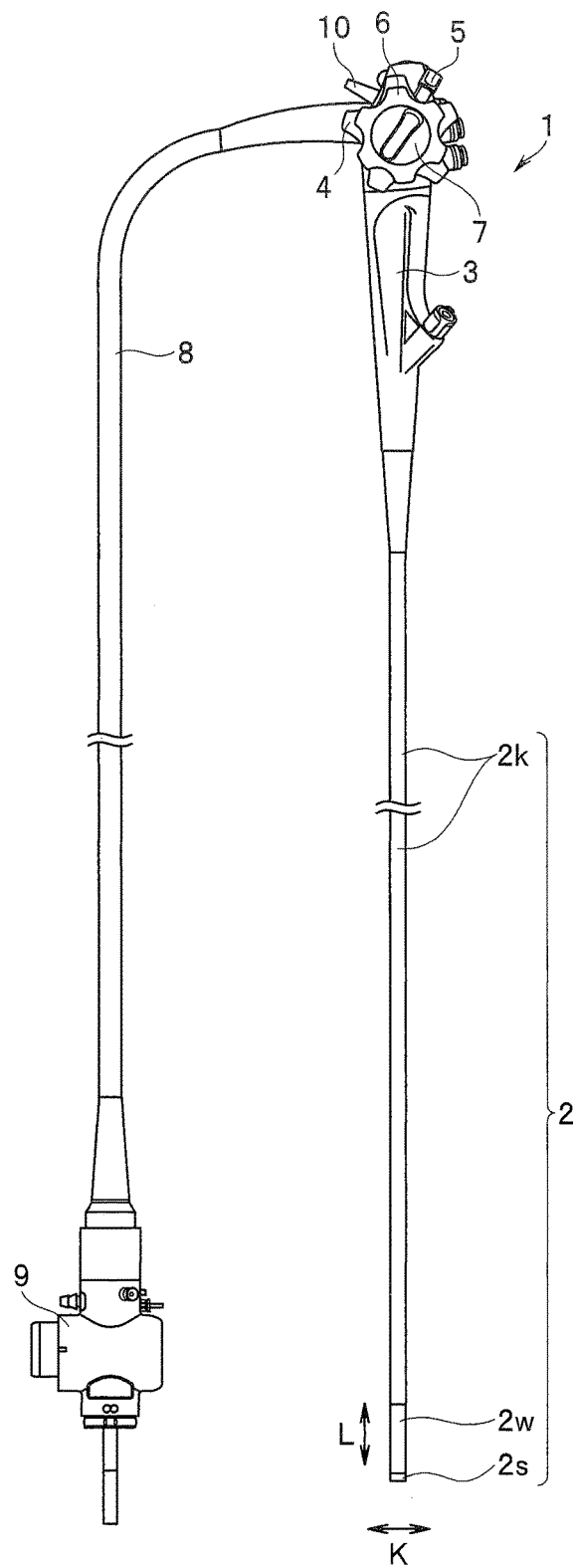
FIG. 1 is a diagram illustrating an appearance of an endoscope including an image pickup apparatus according to a first embodiment.

FIG. 1 is a diagram illustrating an appearance of an endoscope including an image pickup apparatus according to the present embodiment.

As illustrated in FIG. 1, an endoscope 1 includes, as a main part: an insertion section 2 to be inserted into a subject; an operation section 3 connected with a proximal end side of the insertion section 2; a universal cord 8 extended from the operation section 3; and a connector 9 provided on an extended end of the universal cord 8. Note that the endoscope 1 is electrically connected, through the connector 9, with external devices such as a control device and an illumination device.

The operation section 3 includes a vertically bending operation knob 4 that bends a bending portion 2w described later of the insertion section 2 in a vertical direction, and a laterally bending operation knob 6 that bends the bending portion 2w in a lateral direction.

Also, the operation section 3 includes a fixing lever 5 that fixes a pivot position of the vertically bending operation knob 4, and a fixing knob 7 that fixes a pivot position of the laterally bending operation knob 6.

Further, the operation section 3 includes a zoom lever 10 that moves a movable lens frame 40 of an actuator 100 of an image pickup apparatus 101 described later (both refer to FIG. 2).

The insertion section 2 is configured to include a distal end portion 2s, the bending portion 2w, and a flexible tube part 2k in order from the distal end side, and is formed in an elongated.

The bending portion 2w changes an observation direction of the image pickup apparatus 101 described later that is provided inside the distal end portion 2s or improves insertion property of the distal end portion 2s in the subject, for example, by being bent in four directions of vertical and lateral directions through pivot operation of the vertically bending operation knob 4 and the laterally bending operation knob 6. Further, the flexible tube part 2k is connected with a proximal end side of the bending portion 2w.

The image pickup apparatus 101 described later is provided inside the distal end portion 2s that is connected with the distal end side of the bending portion 2w.

The image pickup apparatus 101 includes: the actuator 100 described later; a plurality of unillustrated lenses that are located backward of the actuator 100 in an optical axis direction L (hereinafter, simply referred to backward); and an unillustrated image pickup device that is located backward of the lenses and picks up an image of an object through the actuator 100 and the plurality of lenses. Examples of the image pickup device may include a CCD.

Figure 2:
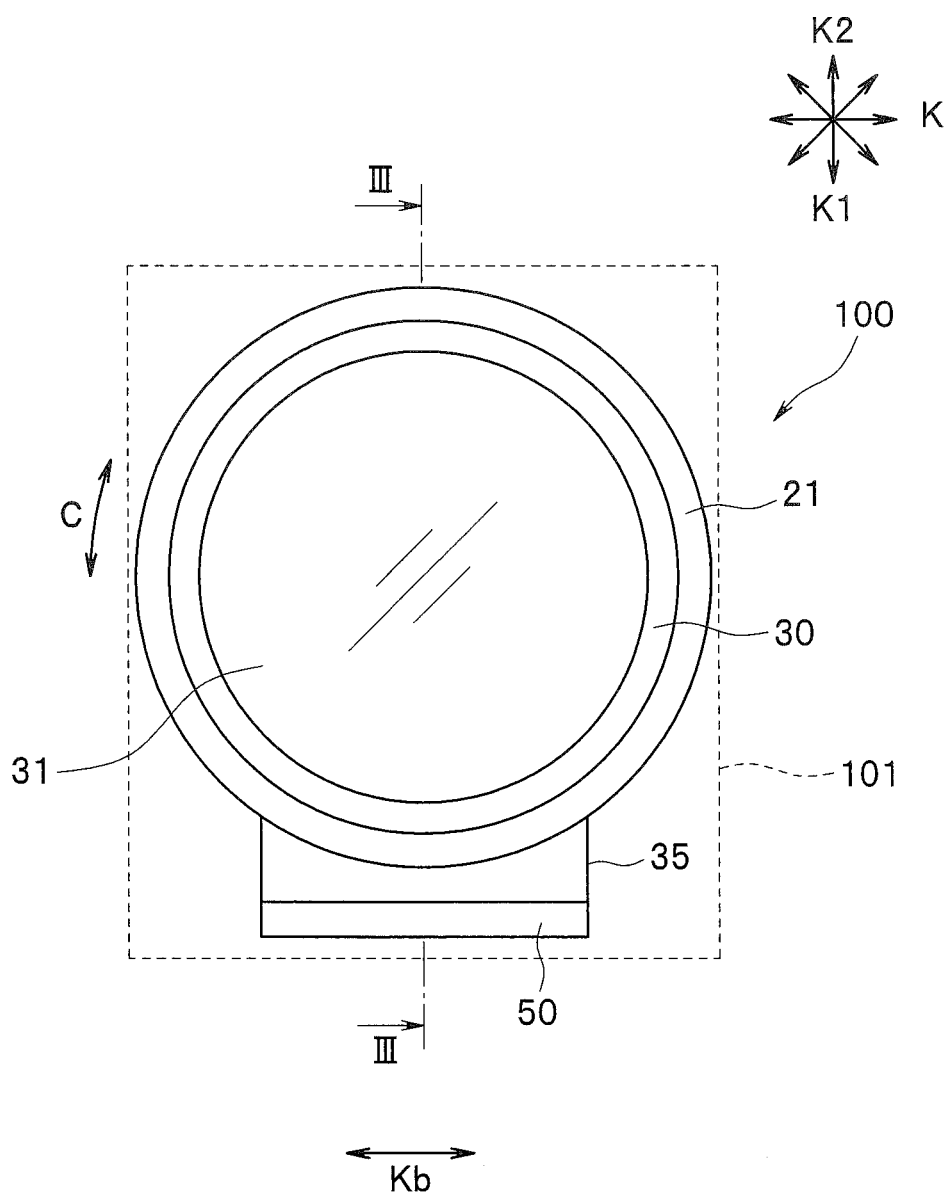
FIG. 2 is a front view of the image pickup apparatus that is provided in a distal end portion of an insertion section of the endoscope in FIG. 1.
Figure 3:
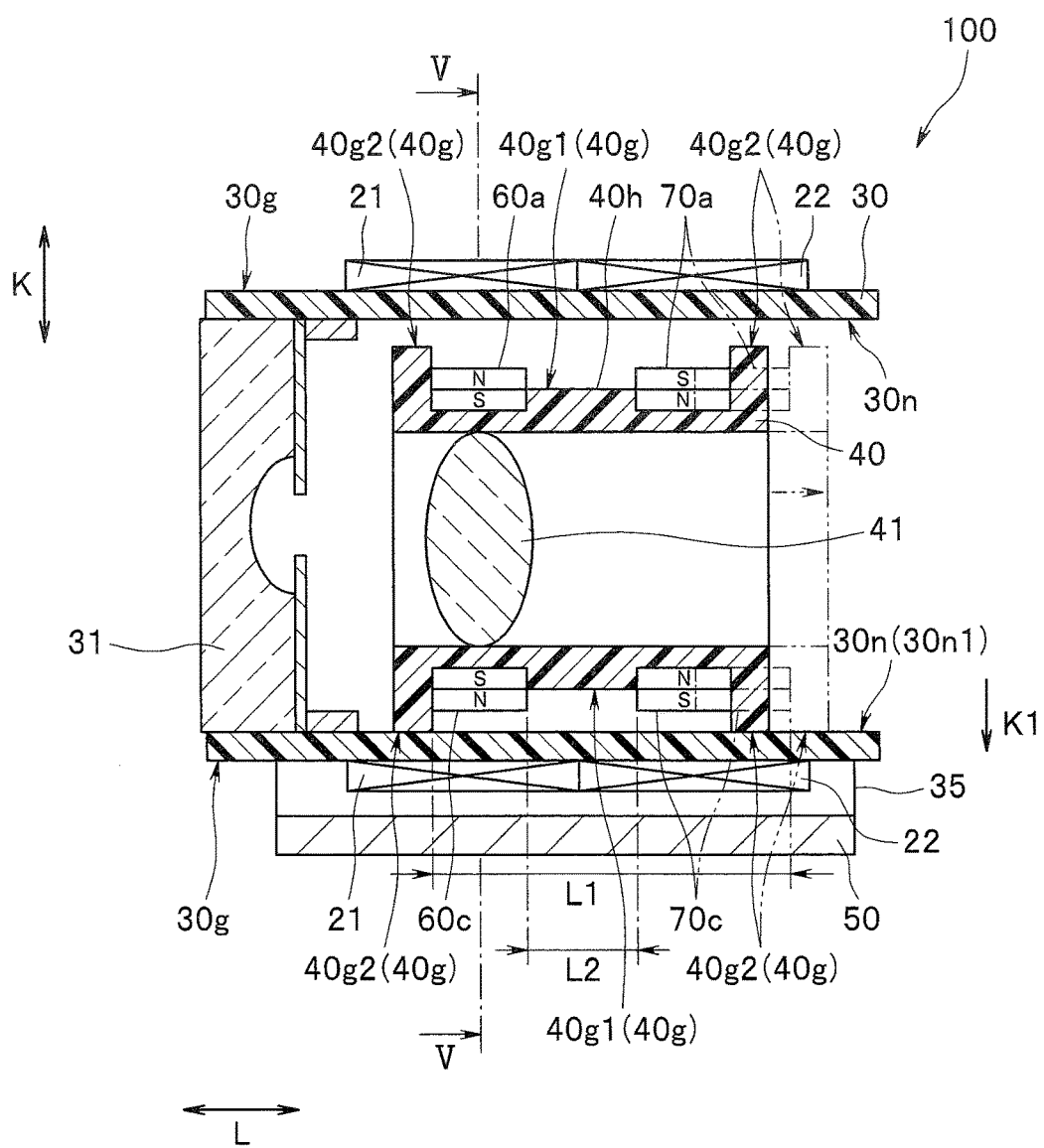
FIG. 3 is a cross-sectional diagram of an actuator taken along line III-III in FIG. 2.
Figure 4:
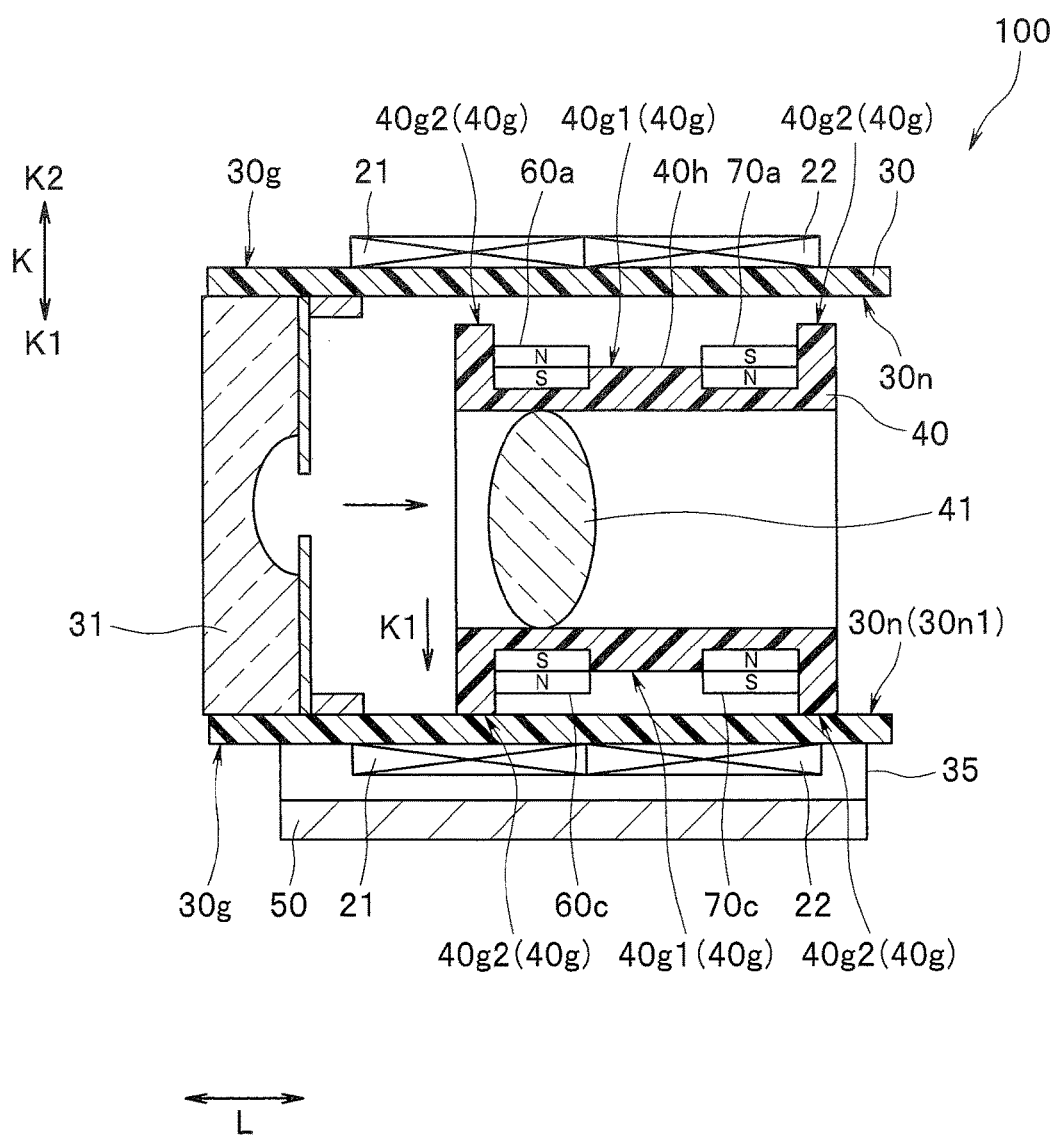
FIG. 4 is a cross-sectional diagram illustrating a state in which a movable lens frame moves backward from a position in FIG. 3, in a holding frame in FIG. 3.
Figure 5:
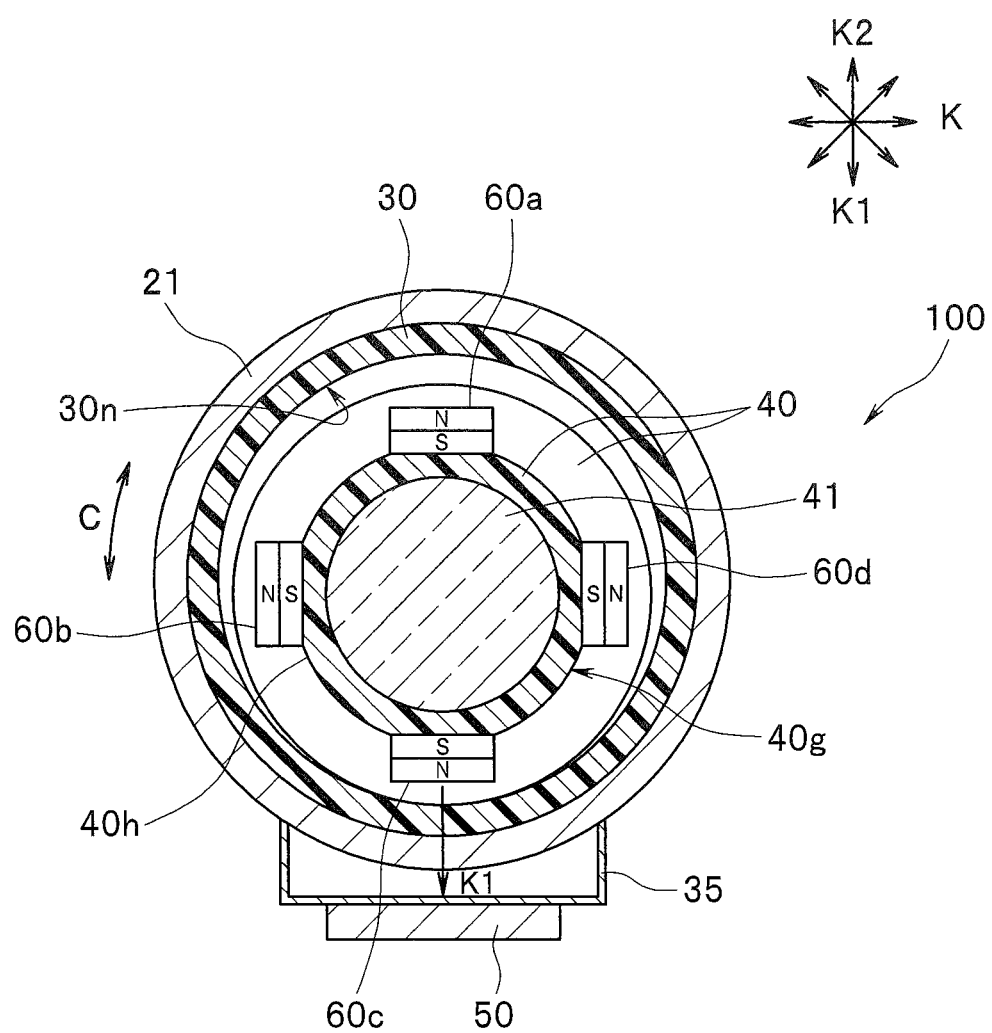
FIG. 5 is a cross-sectional diagram of the actuator taken along line V-V in FIG. 3.

Next, the configuration of the actuator 100 is described with use of FIG. 2 to FIG. 5. FIG. 2 is a front view of the image pickup apparatus that is provided inside the distal end portion of the insertion section of the endoscope in FIG. 1. FIG. 3 is a cross-sectional diagram of the actuator taken along line III-III in FIG. 2. FIG. 4 is a cross-sectional diagram illustrating a state in which the movable lens frame moves backward from a position in FIG. 3, in a holding frame in FIG. 3. FIG. 5 is a cross-sectional diagram of the actuator taken along line V-V in FIG. 3.

As illustrated in FIG. 2 to FIG. 5, the actuator 100 includes, as a main part, a holding frame 30, the movable lens frame 40 as a moving member, and a magnetic member 50.

The movable lens frame 40 internally holds a movable lens 41 that is an optical member. Also, the movable lens frame 40 includes a groove 40h that has a circumferential shape with respect to outer periphery and has a predetermined length along the optical axis direction L.

As illustrated in FIG. 3 to FIG. 5, magnets 60a to 60d are circularly provided along a circumferential direction C on the distal end side of the optical axis direction L (hereinafter, simply referred to as the distal end side) of a part 40g1 formed by the groove 40h in an outer circumferential surface 40g of the movable lens frame 40. Magnets 70a to 70d (magnets 70b and 70d are not illustrated) are circularly provided along the circumferential direction C to be separated backward from the magnets 60a to 60d, on proximal end side in the optical axis direction L (hereinafter, simply referred to as the proximal end side).

Note that the reason why the magnets 60a to 60d and 70a to 70d are provided on the part 40g 1 formed by the groove 40h on the outer circumferential surface 40g is because, if the groove 40h is not provided, the movable lens frame 40 is increased in diameter by the sizes of the magnets 60a to 60d and 70a to 70d in a radial direction K that is orthogonal to the optical axis direction L.

Also, as illustrated in FIG. 5, the magnets 60a to 60d are provided on the outer circumferential surface 40g at substantially 90 degrees intervals in the circumferential direction C. Note that, although not illustrated, the magnets 70a to 70d are also provided on the outer circumferential surface 40g at substantially 90 degrees intervals in the circumferential direction C.

As illustrated in FIG. 5, in the radial direction K, inner parts of the respective magnets 60a to 60d are magnetized with S-pole, and outer parts are magnetized with N-pole.

Also, although only the magnets 70a and 70c are illustrated in FIG. 3 and FIG. 4, inner parts of the respective magnets 70a to 70d are magnetized with N-pole, and outer parts are magnetized with S-pole, in the radial direction K. In other words, the magnets 60a to 60d and the magnets 70a to 70d are opposite in magnetization direction to each other.

Note that the inner parts of the respective magnets 60a to 60d may be magnetized with N-pole and the outer parts may be magnetized with S-pole, and the inner parts of the respective magnets 70a to 70d may be magnetized with S-pole, and the outer parts may be magnetized with N-pole as long as the magnets 60a to 60d and the magnets 70a to 70d are opposite in magnetization direction to each other.

The holding frame 30 is formed in an elongated tubular shape along the optical axis direction L, and holds an objective lens 31 in a distal end in the optical axis direction L (hereinafter, simply referred to as the distal end). Further, the holding frame 30 is located to face the magnets 60a to 60d and the magnets 70a to 70d.

Also, as illustrated in FIG. 3 and FIG. 4, the holding frame 30 internally holds the movable lens frame 40 movably forward and backward in the optical axis direction L (hereinafter, referred to as forward and backward) at the backward of the objective lens 31. Note that a gap is provided between an inner circumferential surface 30n of the holding frame 30 and the outer circumferential surface 40g of the movable lens frame 40, to allow the movable lens frame 40 to be movable in the optical axis direction L.

Further, coils 21 and 22 are circumferentially wound on an outer circumferential surface 30g of the holding frame 30 within a movable range L1 of the magnets 60a to 60d and the magnets 70a to 70d in the optical direction L. The coils 21 and 22 each generate driving force for the movable lens frame 40, in response to energization. In other words, the coils 21 and 22 are provided to face the magnets 60a to 60d and the magnets 70a to 70d, with the holding frame 30 in between.

Note that, on the outer circumferential surface 30g, the coil 21 is wound on the distal end side from the coil 22. Further, the coil 21 is wound in a direction opposite to a winding direction of the coil 22, and a direction of a current flowing through the coil 21 is accordingly opposite to a direction of a current flowing through the coil 22.

Thus, when the currents different in flowing direction flow through the coils 21 and 22, driving force generated for the magnets 60a to 60d and the magnets 70a to 70d acts in the same direction due to Fleming's left-hand rule because the magnetization direction of the magnets 60a to 60d is opposite to that of the magnets 70a to 70d. Then, switching over the directions of the currents flowing through the coil 21 and coil 22 causes the movable lens frame 40 to move forward or backward in the holding frame 30, as illustrated in FIG. 3 and FIG. 4. A focal point of the endoscope 1 on the object is switched over according to the movement of the movable lens frame 40.

Note that the reason why the four magnets 60a to 60d and the four magnets 70a to 70d are uniformly provided on the part 40g1 of the outer circumferential surface 40g at substantially 90 degrees intervals in the circumferential direction C is to uniform magnetic force that is applied from the circumferential coils 21 and 22 to the magnets 60a to 60d and 70a to 70d, in all circumferential direction of the part 40g1 of the outer circumferential surface 40g, namely, in a plurality of directions configuring the radial direction K.

Thus, taking this into consideration, three magnets may be respectively provided on forward side and backward side of the part 40g1 of the outer circumferential surface 40g uniformly at substantially 120 degrees intervals in the circumferential direction C. Alternatively, five or more magnets may be uniformly provided, or magnets may be formed in a circumferential shape.

Note that, since the moving configuration of the movable lens frame 40 in the optical axis direction L using the coils 21 and 22 and the magnets 60a to 60d and 70a to 70d is well-known, the detailed description of the configuration is omitted.

The magnetic member 50 may have, for example, a flat plate shape. As illustrated in FIG. 2 to FIG. 5, the magnetic member 50 is so provided on the outside of the outer circumferential surface 30g of the holding frame 30 and the coils 21 and 22 in the radial direction K as to face the magnets 60c and 70c and to be separated from the outer circumferential surface 30g, only in one direction K1 of the plurality of directions configuring the radial direction K, thereby generating attracting force with respect to the magnets 60c and 70c. The magnetic member 50 may be held by, for example, a holding member 35 fixed to the outer circumferential surface 30g.

Note that the magnetic member 50 may not be held by the holding member 35 fixed to the outer circumferential surface 30g, and may be fixed to other member inside the distal end portion 2s. Also, the shape of the cross-sectional surface of the magnetic member 50 orthogonal to a longitudinal direction is not limited to the rectangular flat plate shape, and the magnetic member 50 may be formed of a rod-shaped member that has, for example, a triangular, circular, or U-shaped cross-sectional surface.

Also, the one direction of the radial direction K is not limited to the direction K1, and may be another direction that faces the magnets 60a to 60d and 70a to 70d.

The magnetic member 50 generates attracting force with respect to the magnets 60c and 70c, thereby pressing a part 40g2 that is not provided with the groove 40h, of the outer circumferential surface 40g of the movable lens frame 40 against a part 30n1, on the direction K1 side, of the inner circumferential surface 30n of the holding frame 30.

This causes the movable lens frame 40 to move forward and backward in the optical axis direction L while the part 40g2 of the outer circumferential surface 40g is pressed against the part 30n1 on the direction K1 side of the inner circumferential surface 30n, as illustrated in FIG. 3 and FIG. 4.

Note that magnitude of the attracting force of the magnetic member 50 with respect to the magnets 60c to 70c is adjustable by varying the width of the magnetic member 50 in a direction Kb of the radial direction K and a distance between the magnetic member 50 and each of the magnets 60c and 70c in the radial direction K. In other words, to reduce the attracting force, the width of the magnetic member 50 in the direction Kb may be decreased or the magnetic member 50 may be moved away from the magnets 60c and 70c.

In addition, the magnetic member 50 may preferably have a length in the optical axis direction L to cover at least the movable range L1 of the magnets 60a to 60d and the magnets 70a to 70d that move together with the movable lens frame 40 in the optical axis direction L.

This is because, when the magnetic member 50 has the length as described above, the magnets 60c and 70c surely face the magnetic member 50 and receive the attracting force from the magnetic member 50, irrespective of before and after the movement of the movable lens frame 40 illustrated in FIG. 3 and FIG. 4.

Note that, when the magnetic member 50 has a length shorter than the movable range L1 in the optical axis direction L, the attracting force from the magnetic member 50 to the magnet 60c and the magnet 70c may become unstable depending on the position of the movable lens frame 40. As illustrated in FIG. 3, however, when the magnetic member 50 is formed to have at least a length L2 between the proximal ends of the magnets 60a to 60d and the distal ends of the magnets 70a to 70d in the optical axis direction L, it is possible to apply, to some extent, the attracting force from the magnetic member 50 to the magnet 60c and the magnet 70c that move in the optical axis direction L.

Also, since the movable lens frame 40 moves in a state in which the part 40g2 of the outer circumferential surface 40g is pressed, by the magnetic member 50, against the part 30n1 on the direction K1 side of the inner circumferential surface 30n, the posture of the movable lens frame 40 becomes stable in movement. Thus, when the magnetic member 50 is in proximity to the outer circumferential surface 30g or when the magnetic member 50 is formed long in the direction Kb, the number of the magnets provided on the forward side and the backward side of the part 40g1 of the outer circumferential surface 40g may be one or two.

As mentioned above, in the present embodiment, in the actuator 100 of the image pickup apparatus 101, the magnetic member 50 that generates the attracting force with respect to the magnets 60c and 70c is disposed to face the magnets 60c and 70c with a distance from the outer circumferential surface 30g only in the direction K1 of the radial direction K, on the outside of the outer circumferential surface 30g of the holding frame 30.

Accordingly, when generating the attracting force with respect to the magnets 60c and 70c, the magnetic member 50 presses the part 40g2 of the outer circumferential surface 40g of the movable lens frame 40 against the part 30n1, on the direction K1 side, of the inner circumferential surface 30n of the holding frame 30. Thus, as illustrated in FIG. 3 and FIG. 4, the movable lens frame 40 moves forward and backward in the optical axis direction L, in a state in which the part 40g2 of the outer circumferential surface 40g is pressed against the part 30n1 on the direction K1 side.

Thus, even if a gap is provided between the inner circumferential surface 30n of the holding frame 30 and the outer circumferential surface 40g of the movable lens frame 40, the movable lens frame 40 moves forward and backward inside the holding frame 30 without backlash, by a simple configuration provided with only the magnetic member 50.

Accordingly, it is possible to provide the image pickup apparatus 101 and the endoscope 1 that surely prevent backlash of the movable lens frame 40 during movement at low cost while achieving downsizing of the movable lens frame 40.

Second Embodiment

Figure 6:
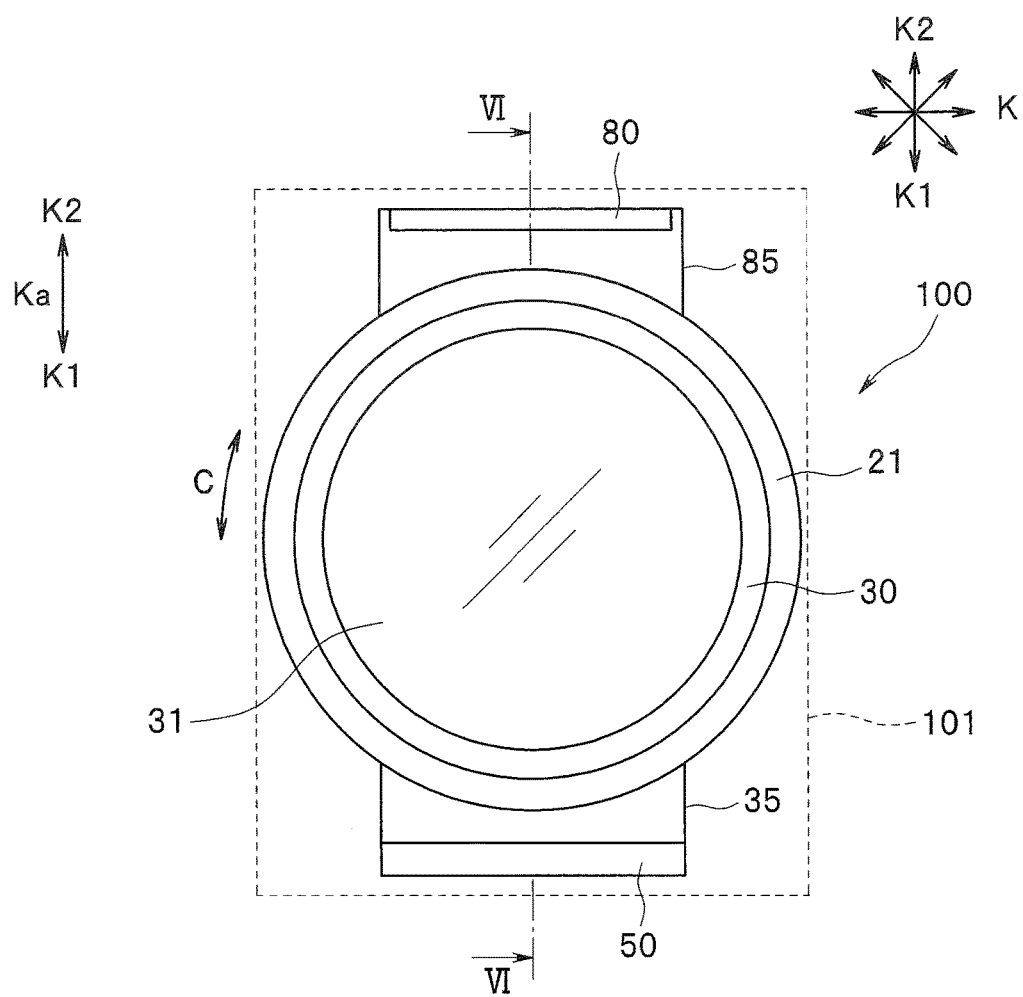
FIG. 6 is a front view of an image pickup apparatus according to a second embodiment.
Figure 7:
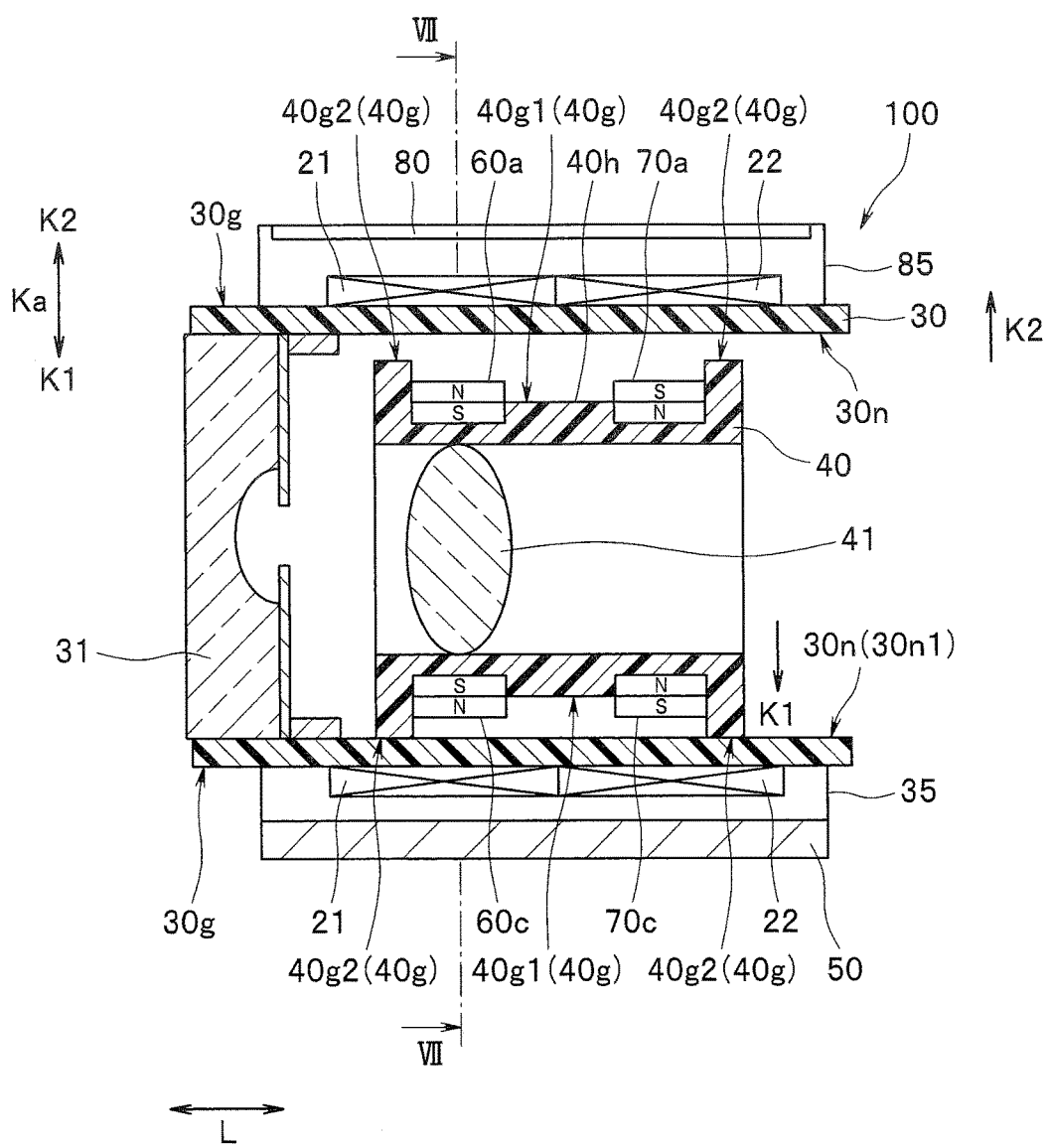
FIG. 7 is a cross-sectional diagram illustrating an actuator taken along line VI-VI in FIG. 6.
Figure 8:
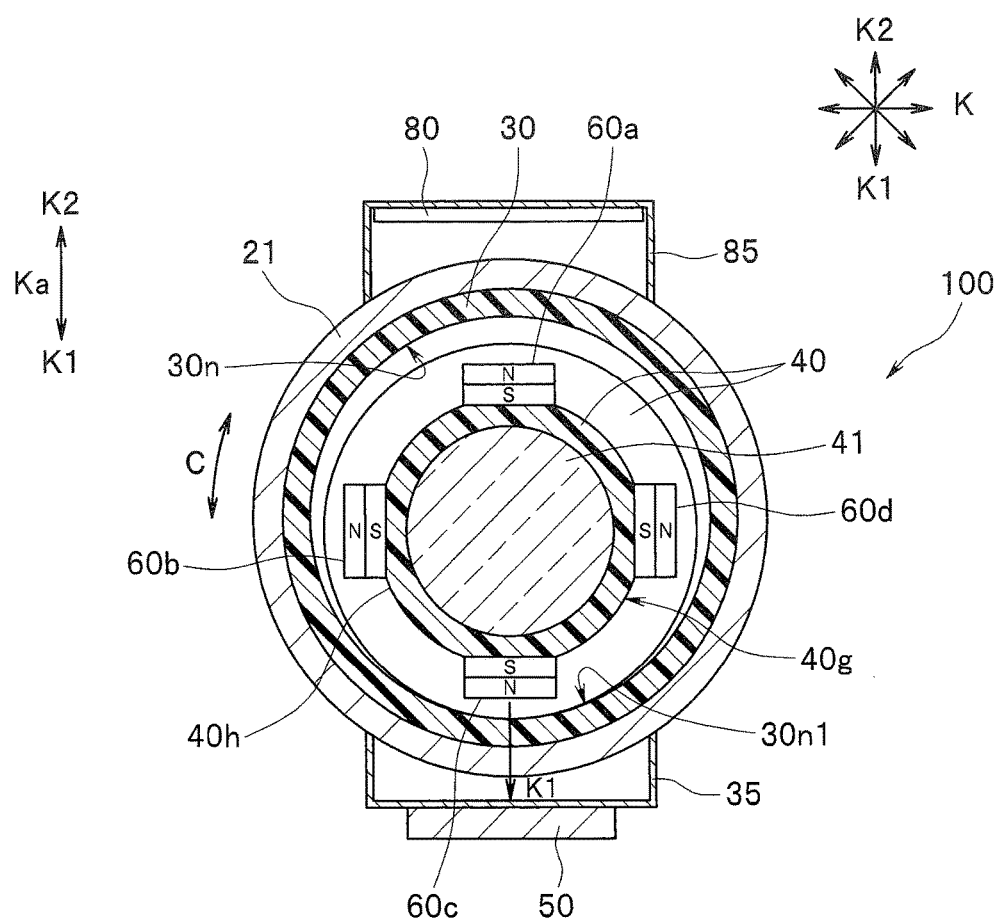
FIG. 8 is a cross-sectional diagram illustrating the actuator taken along line VII-VII in FIG. 7.

FIG. 6 is a front view of an image pickup apparatus according to the present embodiment. FIG. 7 is a cross-sectional diagram of an actuator taken along line VI-VI in FIG. 6. FIG. 8 is a cross-sectional diagram of the actuator taken along line VII-VII in FIG. 7.

Figure 9:
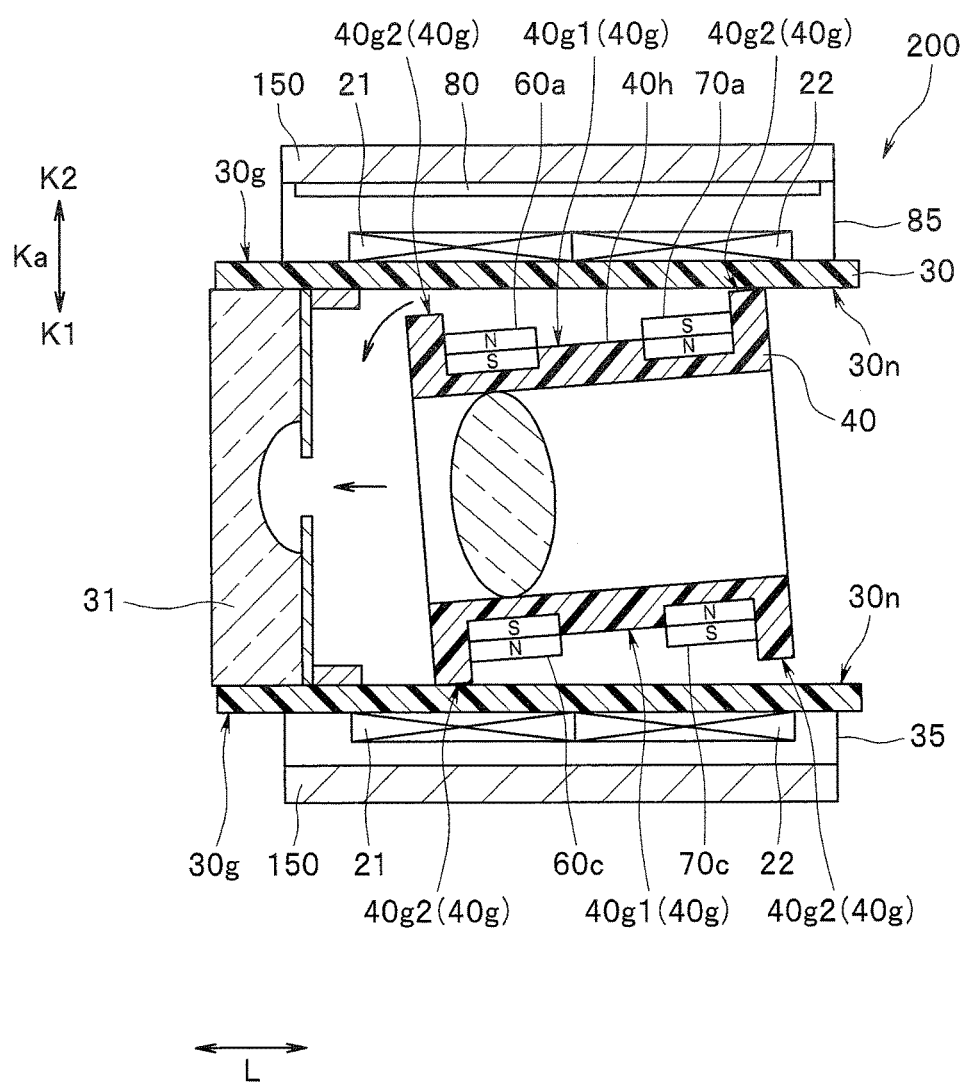
FIG. 9 is a cross-sectional diagram illustrating a state in which a movable lens frame advances in a holding frame in an existing actuator.
Figure 10:
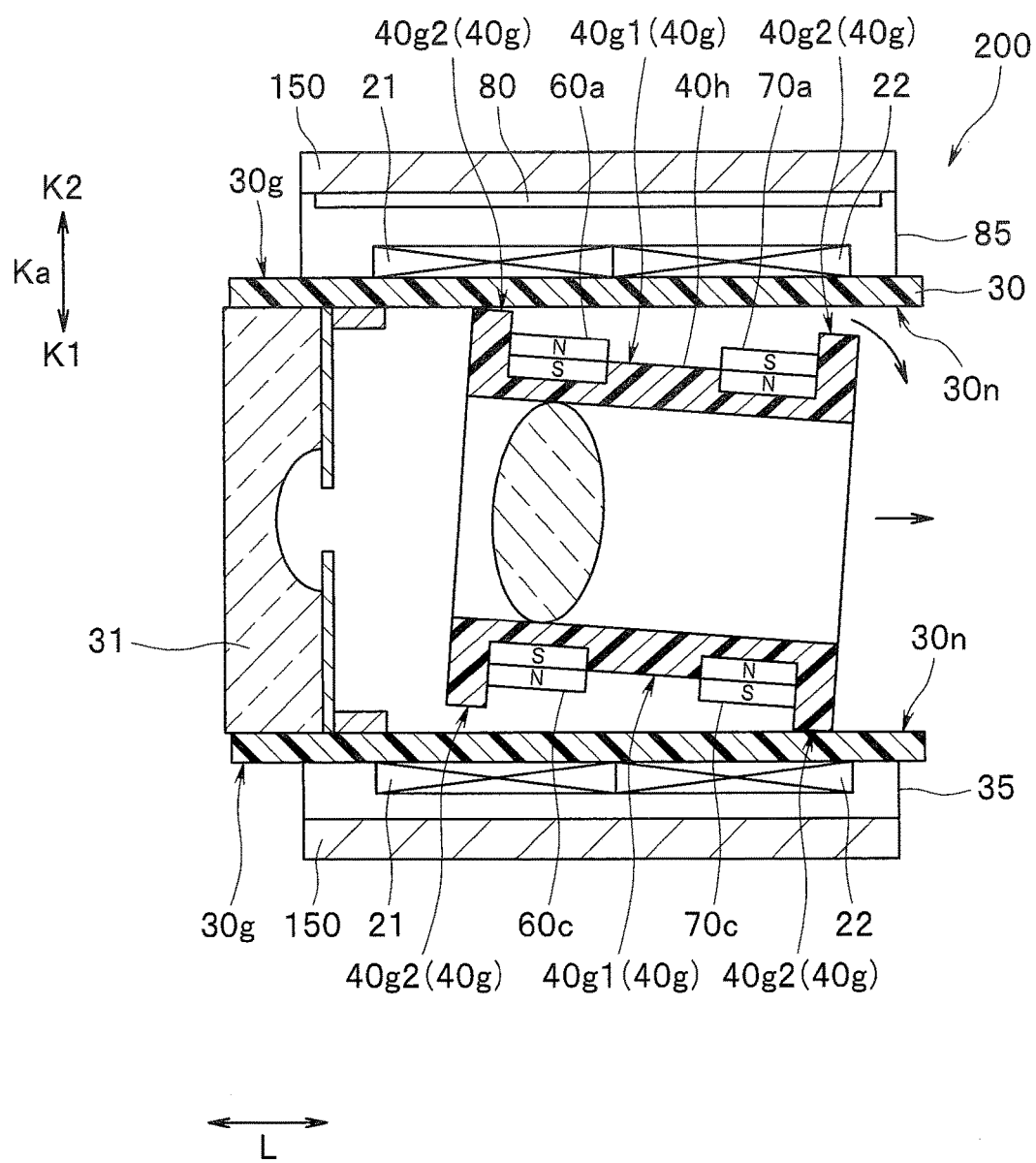
FIG. 10 is a cross-sectional diagram illustrating a state in which the movable lens frame retreats in the holding frame in the existing actuator.

Also, FIG. 9 is a cross-sectional diagram illustrating a state in which a movable lens frame advances in a holding frame in an existing actuator. FIG. 10 is a cross-sectional diagram illustrating a state in which the movable lens frame retreats in the holding frame in the existing actuator.

The configuration of the image pickup apparatus according to the second embodiment is different from the configuration of the image pickup apparatus according to the above-described first embodiment illustrated in FIG. 1 to FIG. 5 in that the actuator includes a sensor that detects a position of the movable lens frame in the optical axis direction.

Thus, only the difference is described, components similar to those of the first embodiment are denoted by the same reference numerals, and description of the components is omitted.

As illustrated in FIG. 6 to FIG. 8, in the actuator 100 of the image pickup apparatus 101 according to the present embodiment, a sensor 80 that detects magnetic force of the magnets 60a and 70a to detect a position of the movable lens frame 40 in the optical axis direction L is provided on the outside of the outer circumferential surface 30g of the holding frame 30 in the radial direction K.

More specifically, the sensor 80 is held by, for example, a holding member 85 that is fixed to the outer circumferential surface 30g of the holding frame 30, so as to face the magnets 60a and 70a, in a direction K2 that is opposite to the direction K1 of the radial direction K.

Note that the sensor 80 may not be held by the holding member 85 that is fixed to the outer circumferential surface 30g, or may be fixed to other member inside the distal end portion 2s. In addition, the sensor 80 may be provided at a position facing any of the magnets 60b to 60d and 70b to 70d.

Also, examples of the sensor 80 may include a well-known Hall element. The Hall element detects variation of the magnitude of the magnetic force according to the movement of the movable lens frame 40 in the optical axis direction L, thereby detecting the position of the movable lens frame 40. Note that, since a principle of detecting the position of the movable lens frame 40 through detection of magnetic force with use of the Hall element is well-known, the detailed description of the principle is omitted.

In the present embodiment, as with the above-described first embodiment, attracting force from the magnetic member 50 acts on the magnets 60c and 70c to press the part 40g2 of the outer circumferential surface 40g of the movable lens frame 40 against the part 30n1 on the direction K1 side. Thus, a distance between the movable lens frame 40 moving forward and backward, more specifically, each of the magnets 60a and 70a and the sensor 80 in a direction Ka of the radial direction K that connects the one direction K1 with the other direction K2 is constantly fixed even during the forward-backward movement of the movable lens frame 40.

The magnetization directions of the magnets 60a and 70a and the coils 21 and 22 are the radial direction K, and the sensor 80 such as the Hall element detects the magnetic force in the direction Ka. Thus, since the distance between each of the magnets 60a and 70a and the sensor 80 is fixed, it is possible to detect the position of the movable lens frame 40 with high accuracy, with use of the sensor 80.

In this case, as illustrated in FIG. 9 and FIG. 10, a configuration in which a cover member 150 is circumferentially provided separately from the outer circumferential surface 30g of the holding frame 30 in the radial direction K is well-known in an existing actuator 200.

In such a configuration of the actuator 200, the magnetic force may not be equivalent between the magnets 60a and 60c, between the magnets 60b and 60d, between the magnets 70a and 70c, and between the magnets 70b and 70d respectively, due to variation in manufacturing or other factor. The part 40g2 of the outer circumferential surface 40g of the movable lens frame 40 inevitably comes into contact with the inner circumferential surface 30n of the holding frame 30.

Also, force occurs on the movable lens frame 40 in the radial direction K orthogonal to the optical axis direction L, due to lines of magnetic force of the magnets 60a to 60d and 70a to 70d and positional displacement of the coils 21 and 22.

Further, the magnets 60a to 60d and the magnets 70a to 70d are arranged in two lines along the optical axis direction L in the part 40g1 of the outer circumferential surface 40g of the movable lens frame 40. Thus, the magnetic force occurred between each of the magnets 60a to 60d and 70a to 70d and each of the coils 21 and 22 in the radial direction K is different between the magnets 60a to 60d and the magnets 70a to 70d. This may cause the movable lens frame 40 to incline as illustrated in FIG. 9 or FIG. 10.

Further, as mentioned above, the directions of the currents flowing through the respective coils 21 and 22 are opposite between when the movable lens frame 40 advances as illustrated in. FIG. 9 and when the movable lens frame 40 retreats as illustrated in FIG. 10. As a result, as illustrated in FIG. 9 and FIG. 10, the movable lens frame 40 may oppositely incline and move in the holding frame 30 as illustrated in FIG. 9 and FIG. 10 between advancing and retreating.

Also, it is considered that, to prevent displacement of the movable lens frame 40 from the fixed position while the movable lens frame 40 is held at the fixed position after advancing or retreating, positive and negative currents may be made to repeatedly flow through the coils 21 and 22 within a range not causing the movable lens frame 40 to move in the optical axis direction L. In this case, however, the driving force that is applied to the movable lens frame to some extent may change the inclination amount of the movable lens frame 40 with respect to the optical axis direction L. Also, the image pickup apparatus 101 is used to be inclined in many directions, which may cause inclination of the movable lens frame 40 with respect to the optical axis direction L due to influence of gravity applied to the movable lens frame 40, or the like. In addition, the inclination amount may also vary depending on the usage state or every time the movable lens frame 40 moves. As mentioned above, since the distance between each of the magnets 60a and 70a and the sensor 80 is not fixed in the direction Ka, the positional detection of the movable lens frame 40 with use of the sensor 80 may not be performed accurately.

In the present embodiment, however, even when the movable lens frame 40 is advancing, retreating, or located at the fixed position, the distance between each of the magnets 60a and 70a and the sensor 80 is fixed in the direction Ka by the magnetic member 50. This makes it possible to perform positional detection of the movable lens frame 40 with high accuracy. Note that other effects are the same as those of the above-described first embodiment.

Figure 11:
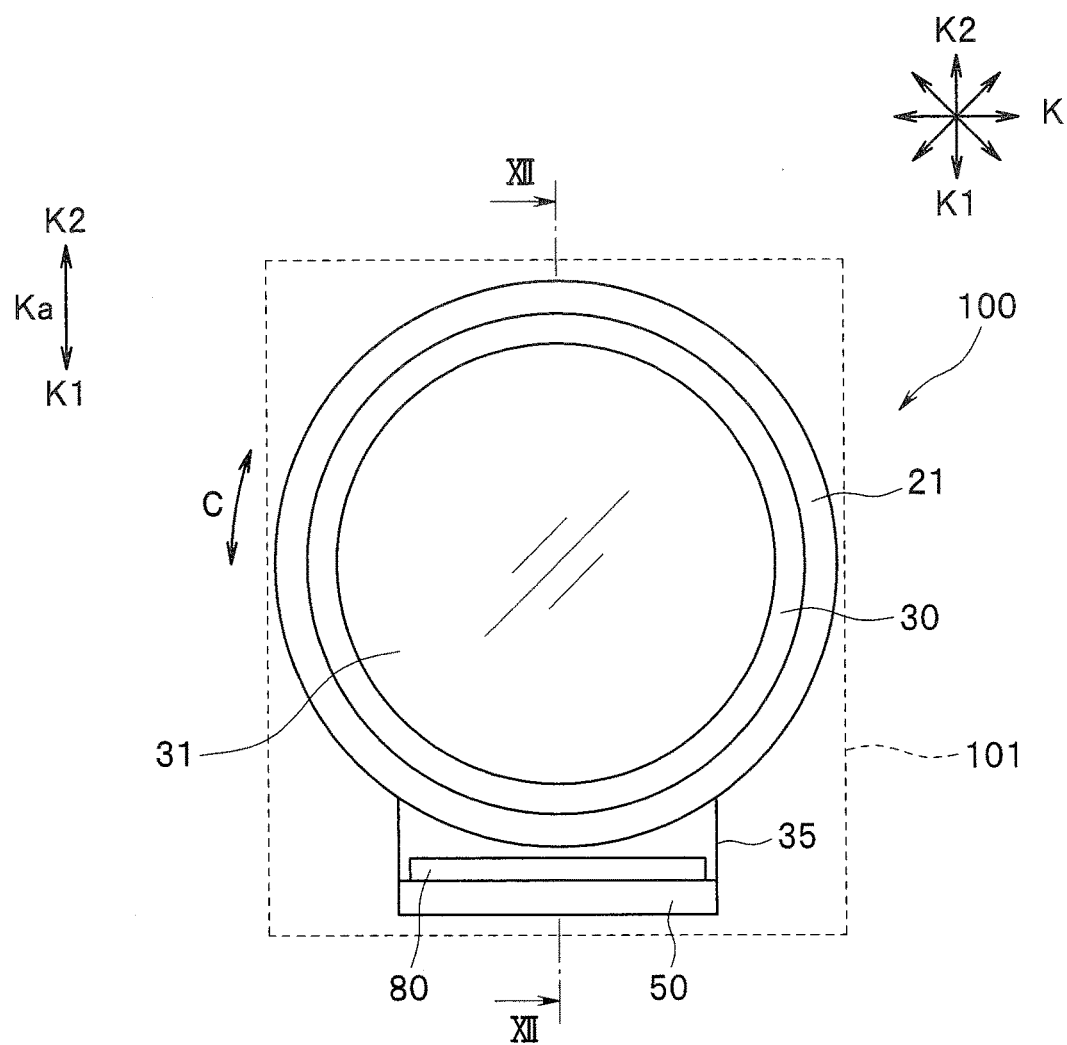
FIG. 11 is a front view illustrating a modification of the image pickup apparatus of FIG. 6.
Figure 12:
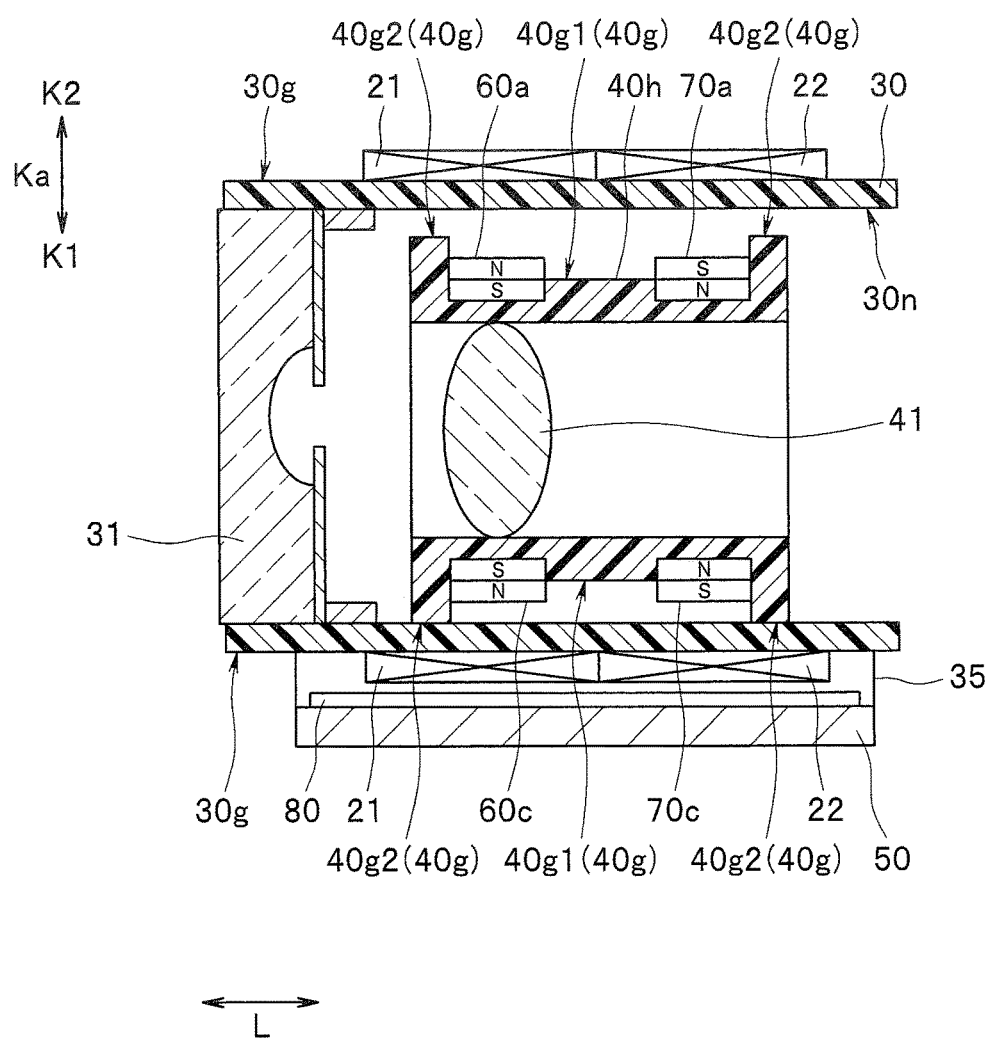
FIG. 12 is a cross-sectional diagram of an actuator taken along line XII-XII in FIG. 11.

Note that a modification is described below. FIG. 11 is a front view illustrating a modification of the image pickup apparatus in FIG. 6. FIG. 12 is a cross-sectional diagram illustrating an actuator taken along line XII-XII in FIG. 11.

As illustrated in FIG. 11 and FIG. 12, the sensor 80 is held on the direction K1 side, more specifically, the sensor 80 is so held, between the magnetic member 50 and the outer circumferential surface 30g of the holding frame 30, by the holding member 35 as to face the magnets 60c and 70c. The sensor 80 may detect magnetic force of the magnets 60c and 70c to detect the position of the movable lens frame 40.

Such a configuration causes the distance between each of the magnets 60c and 70c and the sensor 80 in the direction Ka to be smaller than the distance between each of the magnets 60a and 70a and the sensor 80 in the direction Ka in the above-described embodiment. Thus, it is possible to detect the position of the movable lens frame 40 with higher accuracy than the accuracy of the present embodiment. Note that other effects are the same as those of the above-described embodiment.

Third Embodiment

Figure 13:
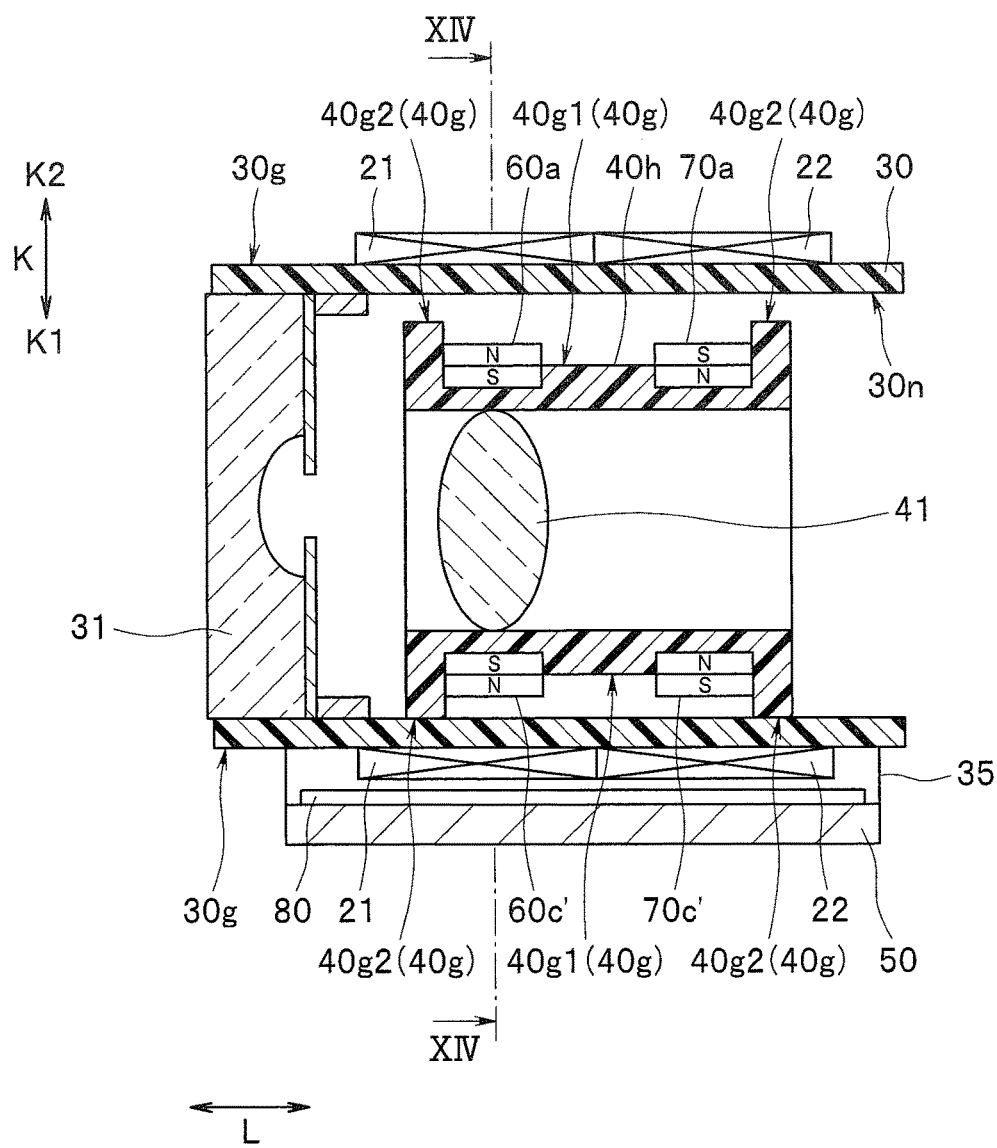
FIG. 13 is a cross-sectional diagram illustrating an actuator of an image pickup apparatus according to a third embodiment.
Figure 14:
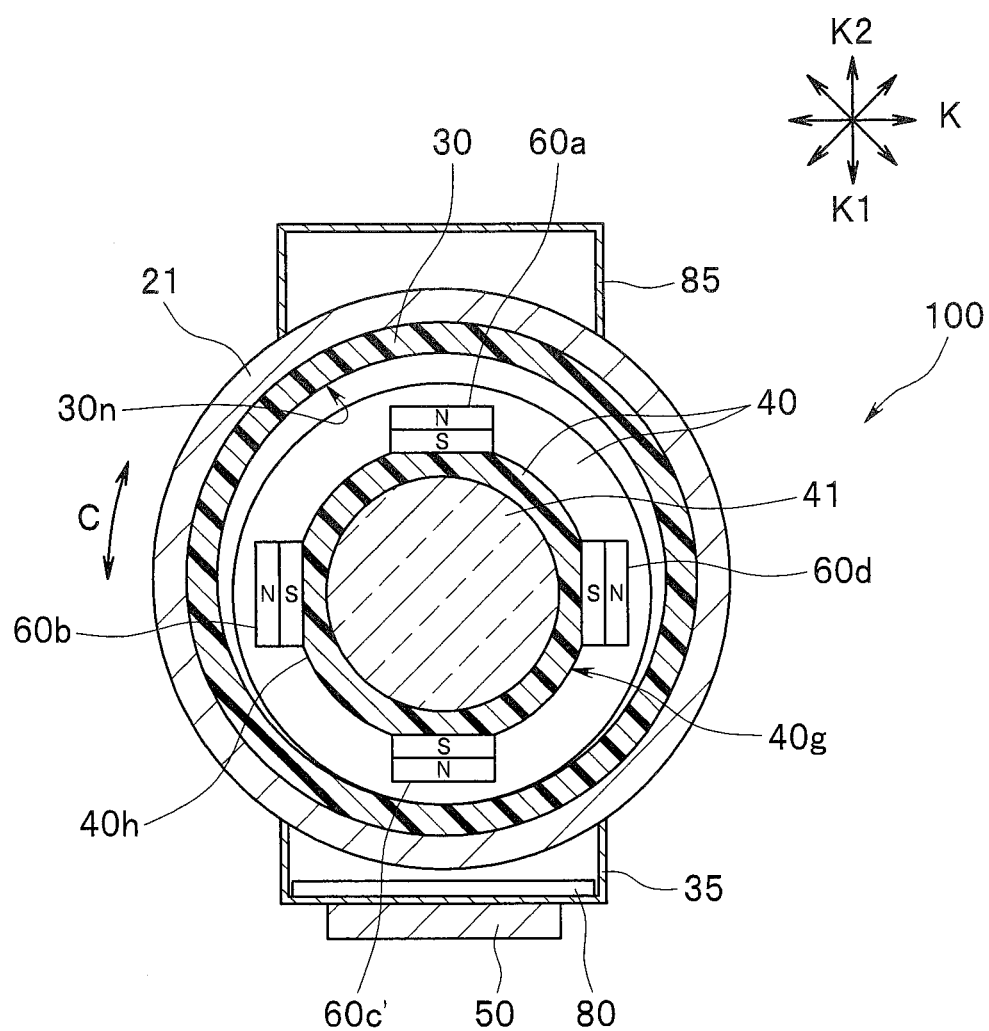
FIG. 14 is a cross-sectional diagram of the actuator taken along line XIV-XIV in FIG. 13.

FIG. 13 is a cross-sectional diagram of an actuator of an image pickup apparatus according to the present embodiment. FIG. 14 is a cross-sectional diagram of the actuator taken along line XIV-XIV in FIG. 13.

The configuration of the image pickup apparatus according to the third embodiment is different from the above-described configuration of the image pickup apparatus according to the second embodiment illustrated in FIG. 6 to FIG. 8, FIG. 11, and FIG. 12 in that, out of a plurality of magnets provided circularly on the outer circumferential surface of the movable lens frame, a magnet, magnetic force of which is detected by a sensor, is formed of a material that has a rate of magnetic force variation caused by temperature variation lower than the rate of magnetic force variation of the material for the other magnets.

Thus, only the difference is described, components similar to those of the second embodiment are denoted by the same reference numerals, and the description of the components is omitted.

As illustrated in FIG. 13 and FIG. 14, out of the magnets 60a, 60b, 60c', 60d, 70a, 70b, 70c' and 70d (the magnets 70b and 70d are not illustrated) that are provided on the part 40g1 of the outer circumferential surface 40g of the movable lens frame 40, the magnets 60c' and 70c' that face the sensor 80 and magnetic force of which is detected by the sensor 80 serve as first magnets, and the magnets 60a, 60b, 60d, 70a, 70b, and 70d serve as second magnets. In this case, the magnets 60a, 60b, 60d, 70a, 70b, and 70d function as driving magnets to cause the movable lens frame 40 to move forward or backward with use of the magnetic force with the coils 21 and 22.

The magnets 60c' and 70c' function as driving magnets and detection magnets, magnetic force of which is detected by the sensor 80.

More specifically, the magnets 60c' and 70c' are each formed of a material that has a rate of magnetic force variation caused by temperature variation lower than the rate of magnetic force variation of the material for the magnets 60a, 60b, 60d, 70a, 70b, and 70d.

More specifically, the magnets 60c' and 70c' are each formed of a samarium cobalt magnet, and the magnets 60a, 60b, 60d, 70a, 70b, and 70d are each formed of a neodymium magnet.

Note that a magnet having a small rate of magnetic force variation caused by temperature variation is typically regarded as a magnet with high temperature characteristics, and a magnet having a large rate of magnetic force variation caused by temperature variation is typically regarded as a magnet with low temperature characteristics.

Also, it is known that the temperature characteristics of the magnet are varied depending on the size and a content of rare earths. The samarium cobalt magnet is higher in temperature characteristics than the neodymium magnet even if the size and the content of rare earths are different between the samarium cobalt magnet and the neodymium magnet.

In contrast, the neodymium magnet is suitable for driving because of having characteristics of extremely strong magnetic force, through the temperature characteristics are not high though, as is well-known. Note that the samarium cobalt magnet may be also used to drive the movable lens frame 40 because the samarium cobalt magnet has strong magnetic force, this is lower than the magnetic force of the neodymium magnet, though.

According to such a configuration, the magnets 60c' and 70c' facing the sensor 80 are each formed of a magnet with high temperature characteristics. Thus, even if the temperature variation is applied to the image pickup apparatus 101, the detection accuracy of the sensor 80 is not impaired because the rate of the magnetic force variation is small.

This is because the endoscope 1 in which the image pickup apparatus 101 is provided may be placed under extremely low or high temperature depending on transportation environment. In addition, in the distal end portion 2s in which the image pickup apparatus 101 is provided, temperature increase caused by heat generation of the coils 21 and 22, heat generation of the other circuit substrate, and heat generation by a light source, and drastic temperature decrease due to water feeding operation may occur. Thus, when the magnet detected by the sensor 80 is formed of a neodymium magnet, the detection accuracy of the sensor may be deteriorated due to variation of the magnetic force according to the temperature variation.

When all of the magnets are formed of samarium cobalt magnets, however, driving force of the movable lens frame 40 is lower than driving force in a case of using a neodymium magnet, which is not favorable. Accordingly, in the present embodiment, only the magnets 60c' and 70c' detected by the sensor 80 are each formed of a samarium cobalt magnet.

Note that, as mentioned above, since the magnetic force is different between the neodymium magnet and the samarium cobalt magnet, the movable lens frame 40 may lose the posture in the holding frame 30. Also in the present embodiment, the magnetic member 50 applies attracting force to the magnets 60c' and 70c', which prevents backlash of the movable lens frame 40 with the movement.

Also, since the magnets 60c' and 70c' function not only as detection magnets but also as driving magnets, an additional detection magnet is unnecessary in addition to the driving magnet. This makes it possible to achieve downsizing of the movable lens frame 40. Note that other effects are similar to those of the above-described second embodiment.

Further, also in the present embodiment, the sensor 80 may be provided at a position different from the magnetic member 50 as illustrated in FIG. 6 to FIG. 8 mentioned above. In this case, it is sufficient to form the magnet facing the sensor 80 by a samarium cobalt magnet.

Further, the samarium cobalt magnet has been described as an example of the magnet having high temperature characteristics; however, other magnets having high temperature characteristics may be adopted without limitation.

Figure 15:
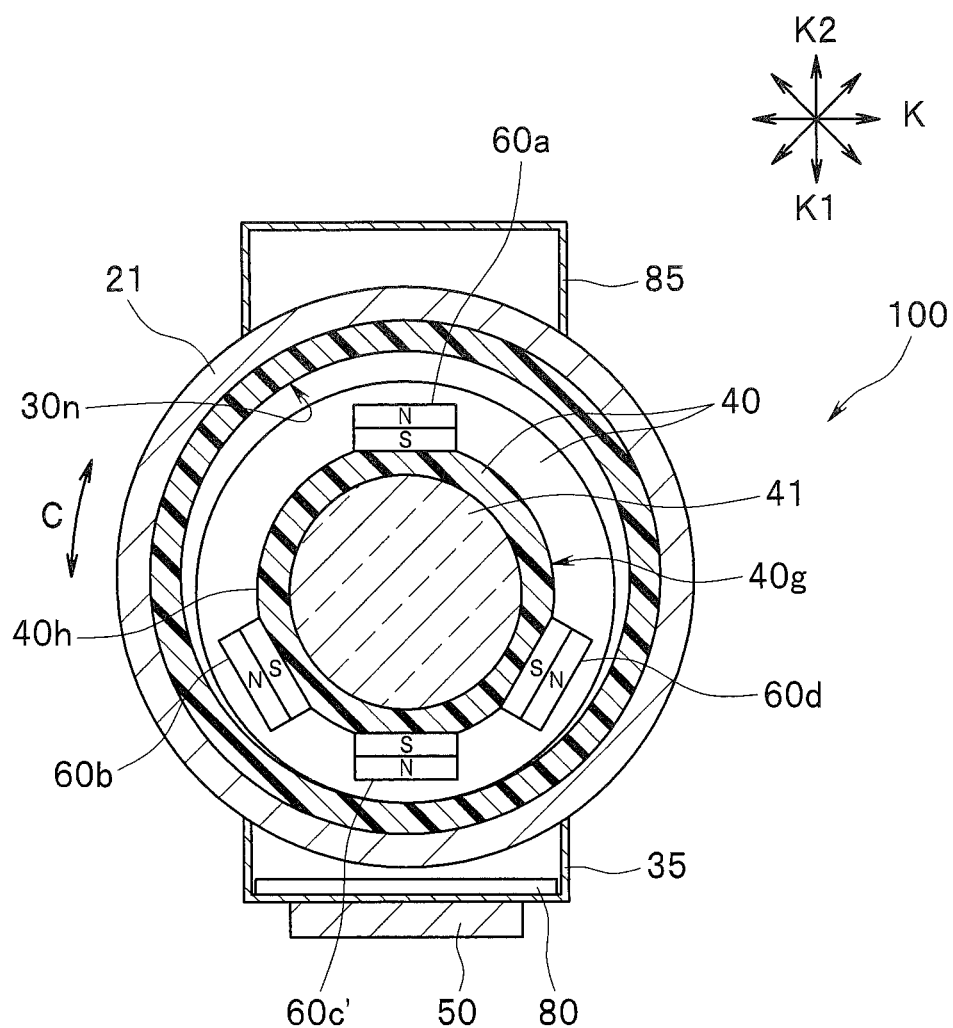
FIG. 15 is a cross-sectional diagram of an actuator illustrating a modification of disposed positions of second magnets in FIG. 14.

Also, a modification is illustrated below with use of FIG. 15. FIG. 15 is a cross-sectional diagram of an actuator illustrating a modification of disposed positions of second magnets in FIG. 14.

As illustrated in FIG. 15, the magnets 60a, 60b, 60d, 70a, 70b, and 70d (the magnets 70a, 70b, 70d are not illustrated) that are second magnets formed of a neodymium and serve as the driving magnets may be arranged on the outer circumferential surface 40g at substantially 120 degrees intervals in the circumferential direction C in order to maintain posture balance of the movable lens frame 40 in movement only by these magnets. The magnets 60c' and 70c' that are first magnets formed of samarium cobalt and serve as the detection magnets may be respectively disposed between the magnets 60b and 60d and between the magnets 70b and 70d. Such a configuration also makes it possible to exert effects similar to those of the present embodiment.

Note that, although the image pickup apparatus 101 is provided in the endoscope 1 in the above-described first to third embodiments, the configuration is not limited to those described in the first to third embodiments, and the image pickup apparatus 101 is applicable to a case of being provided in a camera or the like.

According to the present invention, it is possible to provide the image pickup apparatus and the endoscope that surely prevent backlash of the movable lens frame during movement at low cost while achieving downsizing of the movable lens frame.

The present invention is not limited to the above-described embodiments, and is variously modified, altered or the like within the scope of the invention.

What is claimed is:

1. An image pickup apparatus, comprising:
a lens frame internally holding a movable lens, and including a magnet provided on an outer circumferential surface;
a holding frame holding an objective lens on a distal end, internally holding the lens frame movably in an optical axis direction of the movable lens, and including a coil that is wound on an outer circumferential surface, the coil being provided to face the magnet and generating driving force with respect to the lens frame in response to energization; and
a magnetic member provided on outside of the outer circumferential surface of the holding frame in a radial direction of the holding frame that is orthogonal to the optical axis direction, the magnetic member facing the magnet only in one direction of a plurality of directions configuring the radial direction, and the magnetic member generating attracting force with respect to the magnet, wherein
the magnet includes a plurality of magnet pairs provided at uniform angles in a circumferential direction of the lens frame, each of the magnet pairs including magnets that are respectively disposed on a distal end side and a proximal end side along the optical axis direction of the movable lens,
the magnet disposed on the distal end side has a polarity opposite in the radial direction to a polarity of the magnet disposed on the proximal end side, and
the magnetic member is provided to face the magnets that configure one of the plurality of magnet pairs.

2. The image pickup apparatus according to claim 1, wherein
the magnetic member generates the attracting force with respect to the magnets that configure the one of the magnet pairs, to press the outer circumferential surface of the lens frame against a part on one direction side of an inner circumferential surface of the holding frame, and
the lens frame moves in the optical axis direction while the outer circumferential surface is pressed against the part on the one direction side of the inner circumferential surface of the holding frame.

3. The image pickup apparatus according to claim 1, wherein the magnetic member extends, in the optical axis direction, to cover at least a movable range of the magnets that configure the one of the magnet pairs and move in the optical axis direction with the lens frame.

4. The image pickup apparatus according to claim 1, further comprising a sensor that detects magnetic force of the magnets configuring the one of the magnet pairs, to detect a position of the lens frame in the optical axis direction, the sensor being provided on outside of the outer circumferential surface of the holding frame in the radial direction.

5. The image pickup apparatus according to claim 4, wherein the sensor is located between the magnetic member and the outer circumferential surface of the holding frame in the radial direction.

6. The image pickup apparatus according to claim 4, wherein
the magnet is provided in plurality on the outer circumferential surface of the lens frame along a circumferential direction of the lens frame, and includes a first magnet that faces the sensor, magnetic force of the first magnet being detected by the sensor, and another second magnet, and
the first magnet is formed of a material that has a rate of magnetic force variation caused by temperature variation smaller than a rate of magnetic force variation of a material of the second magnet.

7. The image pickup apparatus according to claim 6, wherein
the first magnet is formed of a samarium cobalt magnet, and
the second magnet is formed of a neodymium magnet.

8. An endoscope comprising the image pickup apparatus according to claim 1, wherein
the lens frame moves in the optical axis direction to switch over a focal point on an object.

* * * * *